United States Patent [19]

Draper et al.

[11] 4,185,101

[45] Jan. 22, 1980

[54] 1,3,5(10),6,8-19-NOR-PREGNAPENTAENES, THEIR USE AS ANTI-PSORIATIC AGENTS, AND PHARMACEUTICAL FORMULATIONS USEFUL THEREFOR

[75] Inventors: Richard W. Draper, North Caldwell; Michael J. Green, Kendall Park; Charles J. Casmer, Rahway, all of N.J.

[73] Assignee: Schering Corporation, Kenilworth, N.J.

[21] Appl. No.: 925,725

[22] Filed: Jul. 18, 1978

Related U.S. Application Data

[63] Continuation-in-part of Ser. No. 823,573, Aug. 11, 1977, abandoned.

[51] Int. Cl.$^2$ .......................... A61K 31/56; C07J 5/00
[52] U.S. Cl. ................................ 424/243; 260/397.4; 260/397.47; 260/397.45; 260/239.55 D
[58] Field of Search ................................ 424/238, 243

[56] References Cited

U.S. PATENT DOCUMENTS

| | | | |
|---|---|---|---|
| 3,116,289 | 12/1963 | Tanabe | 260/239.55 |
| 3,182,057 | 5/1965 | Heller et al. | 260/397.45 |
| 3,182,075 | 5/1965 | Heller et al. | 260/397.45 |
| 3,282,929 | 11/1966 | Heller et al. | 260/239.55 |

OTHER PUBLICATIONS

Heller et al., J.A.C.S. (1967) vol. 89, pp. 1911–1925.

*Primary Examiner*—Elbert L. Roberts
*Attorney, Agent, or Firm*—Mary S. King

[57] ABSTRACT

1,3,5(10),6,8-19-Nor-pregnapentaene-20-ones exhibit anti-mitotic activity with minimal or no hormonal activity. They are particularly useful in the treatment and control of psoriasis when applied topically, preferred anti-psoriatic compounds being 1,3,5(10),6,8-19-nor-pregnapentaene-3,17α,21-triol-20-one 21-acetate and the 16α-methyl and 16β-methyl analogs thereof.

The 1,3,5(10),6,8-19-nor-pregnapentaene-20-ones are also useful as intermediates in the preparation of the corresponding 14-dehydro compounds which also exhibit anti-mitotic activity as described and claimed in copending application Ser. No. 819,182 filed July 26, 1977 of Richard W. Draper and Charles J. Casmer of common assignee as this application, and now abandoned.

10 Claims, No Drawings

1,3,5(10),6,8-19-NOR-PREGNAPENTAENES, THEIR USE AS ANTI-PSORIATIC AGENTS, AND PHARMACEUTICAL FORMULATIONS USEFUL THEREFOR

CROSS REFERENCE TO RELATED APPLICATION

This application is a continuation-in-part of our copending application Ser. No. 823,573 filed Aug. 11, 1977, and now abandoned.

FIELD OF INVENTION

This invention relates to novel compositions-of-matter, their use as anti-mitotic agents, and pharmaceutical formulations useful therefor.

More specifically, this invention relates to 1,3,5(10),6,8-19-nor-pregnapentaene-20-ones, their use in the treatment and control of psoriasis, and pharmaceutical formulations useful therefor.

PRIOR ART

Described in the art are 1,3,5(10),6,8-19-nor-pregnapentaene-3,17α,21-triol-20-ones and methods for their preparation (M. Heller et al, J. Am. Chem. Soc., 89, 1911–1918 and 1919–1924 (1967) and U.S. Pat. Nos. 3,182,057 and 3,182,075, wherein 11-unsubstituted-19-nor-pregnapentaenes are disclosed as hypoglycemic agents).

By this invention, we have discovered that 1,3,5(10),6,8-19-nor-pregnapentaene-3,17α,21-triol-20-ones exhibit anti-mitotic activity with minimal or no hormonal side effects and, thus, are useful in the treatment of diseases characterized by rapid cell proliferation and/or abnormal cell proliferation; the 19-nor-pregnapentaene-20-ones of this invention being useful in the treatment and control of psoriasis when administered topically.

COMPOSITION-OF-MATTER ASPECT OF THE INVENTION

This invention relates to new pharmaceutical formulations comprising as active ingredient a 1,3,5(10),6,8-19-nor-pregnapentaene-3,17α,21-triol-20-one or derivatives thereof and to the use of such formulations for the treatment and control of diseases characterized by rapid cell proliferation and/or abnormal cell proliferation. Specifically, the pharmaceutical formulations of this invention are particularly useful in the treatment and control of proliferative skin diseases, and are primarily used for the treatment of psoriasis.

Included among the active compounds of the new therapeutic formulations of this invention are 19-nor-pregnapentanene-20-ones defined by formula I:

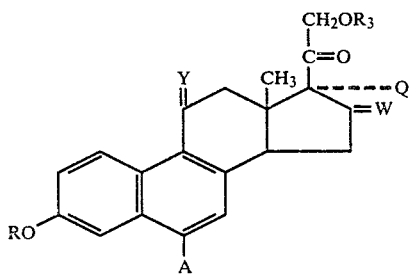

wherein

A is hydrogen, lower alkyl, fluoro, fluoromethyl, difluoromethyl, or trifluoromethyl;

R is hydrogen, lower alkyl, or an acyl radical of a hydrocarboncarboxylic acid having up to 20 carbon atoms;

Y is (H,H), (H,OH), or oxygen;

W is (H,H); (H, lower alkyl); (H,α-hydroxy); (H,α-OR$_1$), wherein R$_1$ is an acyl radical of a hydrocarboncarboxylic acid having up to 20 carbon atoms; or =CHT wherein T is hydrogen, lower alkyl, fluorine, or chlorine;

Q is OR$_2$ wherein R$_2$ is hydrogen or an acyl radical of a hydrocarboncarboxylic acid having up to 20 carbon atoms; hydrogen provided W is (H,H), or (H, lower alkyl); or Q and W together is a 16α,17α-lower alkylidenedioxy;

R$_3$ is hydrogen or an acyl radical of a hydrocarbon-carboxylic acid having up to 20 carbon atoms; or OR$_3$ together with Q is a member selected from the group consisting of alkylidenedioxy and alkylorthoalkanoate;

and when Q is hydroxy and R$_3$ is hydrogen, the 17α,20;20,21-bismethylenedioxy derivatives thereof;

together with a non-toxic pharmaceutically acceptable carrier.

Lower alkyl groups included within the definition of A, R and W are preferably those having up to four carbon atoms such as methyl, ethyl, n-propyl, isopropyl, n-butyl, sec.-butyl, and tert.-butyl, although higher homologs such as pentyl and hexyl fall within the scope of this invention.

As used in the specification and claims of this application, the term "acyl" denotes a radical derived from an acid by removal of a hydroxyl group, e.g. acetyl is the acyl radical of acetic acid; benzoyl is the acyl radical of benzoic acid.

The acyl radicals of the compounds of this invention as defined by R, R$_1$, R$_2$ and R$_3$ in formula I hereinabove include those derived from hydrocarboncarboxylic acids having up to twelve carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms, aryloxy having from 6 to 10 carbon atoms, or by a halogen. Typical ester groups of the 19-nor-pregnapentaenes of the formulations of our invention are thus derived from hydrocarboncarboxylic acids such as alkanoic acids exemplified by acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids; substituted alkanoic acids such as phenoxyacetic, trifluoroacetic, β-chloropropionic acids and β-benzoylaminoisobutyric acids; aromatic and substituted aromatic acids including benzoic, toluic, p-chlorobenzoic, p-fluorobenzoic, p-methoxybenzoic, and 3',5'-dimethylbenzoic acids; aryl-alkanoic acids such as phenylacetic and phenylpropionic; unsaturated acids such as retinoic, farnesyl acetic, acrylic, sorbic and oleic acids; and dibasic acids such as succinic, tartaric, phthalic and benzene disulfonic acids.

Preferred acyl radicals defined by R, R$_1$, R$_2$ and R$_3$ of formula I are those derived from lower alkanoic acids having preferably up to 8 carbon atoms such as radicals obtained from acetic, propionic, butyric, valeric, caprylic, caproic, tert.-butylacetic acid and the like, as well as those derived from aromatic carboxylic acids having up to 8 carbon atoms, preferably benzoic acid.

The alkylidene groups contemplated in the compounds of our invention are preferably lower alkylidenes, i.e. hydrocarbon radicals having preferably up to 4 carbon atoms including radicals such as methylene, ethylidene, n-propylidene, isopropylidene, n-butylidene, and sec.-butylidene and the like. The 16-lower alkylidene derivatives of this invention (i.e. when W in above formula I is =CHT) are double bonded to the D ring at C-16. The 16α,17α-alkylidenedioxy derivatives have the alkylidene terminal bonds attached to different oxygen atoms, i.e. to the oxygens at C-16 and C-17 in the case of the 16α,17α-alkylidenedioxy derivatives, and to oxygens at C-17 and C-21 in the case of the 17α,21-alkylidenedioxy derivatives.

The physical embodiments of the 19-nor-pregnapentaene-20-ones of the formulations of this invention are characterized by being crystalline solids, usually white to off-white in color which are insoluble in water and soluble in most organic solvents, particularly in acetone, dioxane, dimethylformamide, and dimethylsulfoxide, although of limited solubility in non-polar solvents such as dialkylethers and alkylhydrocarbons.

The 19-nor-pregnapentaene-20-ones of formula I exhibit anti-mitotic activity and, in particular, are useful in the treatment and control of psoriasis.

Useful 19-nor-pregnapentaene-20-ones of formula I include 1,3,5(10),6,8-19-nor-pregnapentaene-3,17α,21-triol-20-one 21-acetate and the 6-methyl-, 6-fluoro-, 6-difluoromethyl- and 6-trifluoromethyl- derivatives thereof as well as the 16α-methyl and 16β-methyl analogs thereof, 16α-hydroxy derivatives of formula I and ester and 16α,17α-alkylidenedioxy derivatives thereof such as 1,3,5(10),6,8,-19-nor-pregnapentaene-3,16α,17α,21-tetrol-20-one 16,21-diacetate and 16α,17α-isopropylidenedioxy-1,3,5(10),6,8-19-nor-pregnapentaene-3,21-diol-20-one 21-acetate, and 16-alkylidene derivatives of formula I such as 16-methylene-1,3,5(10),6,8-19-nor-pregnapentaene-3,17α,21-triol-20-one 21-acetate and the 3-acetate and 3-methyl ether derivatives thereof;

11-oxo derivatives of formula I such as

16α-methyl-1,3,5(10),6,8-19-nor-pregnapentaene-3,17α,21-triol-11,20-dione, the 21-acetate thereof, and the 16β-methyl epimers of the foregoing; and 11-hydroxy derivatives of formula I such as 16α-methyl-1,3,5(10),6,8-19-nor-pregnapentaene-3,11β,17α,21-tetrol-20-one, the 21-acetate thereof, the 16β-methyl epimers of the foregoing and the 11α-hydroxy epimers of the foregoing.

Of the compounds of formula I, those particularly useful for the treatment of psoriasis are the 11-oxygenated-1,3,5(10),6,8-19-nor-pregnapentaene-20-ones of formula II:

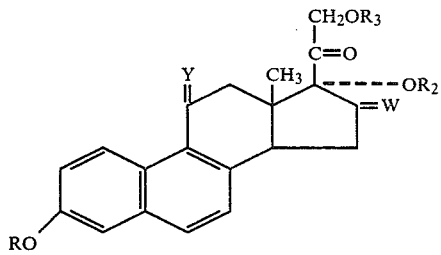

wherein
R is hydrogen, lower alkyl, or an acyl radical of a hydrocarboncarboxylic acid having up to 8 carbon atoms;
$R_2$ and $R_3$ are each hydrogen or an acyl radical of a hydrocarboncarboxylic acid having up to 8 carbon atoms;
Y is (H,OH) or oxygen; and
W is (H,H) or (H,CH$_3$).

Preferred compounds of formula II thus include
1,3,5(10),6,8-19-nor-pregnapentaene-3,17α,21-triol-11,20-dione 21-acetate, the 3-acetate, the 3-benzoate and the 3-methyl ether derivatives thereof;
1,3,5(10),6,8-19-nor-pregnapentaene-3,17α,21-triol-11,20-dione and the 21-propionate, the 17-propionate and 17,21-di-n-butyrate ester derivatives thereof;
the 16α-methyl and 16β-methyl homologs of the foregoing, and the corresponding 11-hydroxy derivatives of all the foregoing.

Of the compounds defined by formula II, particularly useful anti-psoriatic agents are 1,3,5(10),6,8-19-nor-pregnapentaene-3,17α,21-triol-11,20-dione 21-acetate, the 16α-methyl and 16β-methyl homologs thereof and their corresponding 11β-hydroxy derivatives which exhibit anti-mitotic activity at topical doses of 2 mg. when administered topically to mice in which epidermal mitosis has been stimulated by prior application of croton oil.

In addition to exhibiting anti-mitotic activity, the 19-nor-pregnapentaene-20-ones of formula I are useful as intermediates in preparing the corresponding 1,3,5(10),6,8,14-19-nor-pregnahexaene-3,17α,21-triol-20-ones, also useful anti-mitotic agents as claimed in copending application U.S. Ser. No. 823,573 filed Aug. 11, 1977, of common assignee as this application. The 1,3,5(10),6,8,14-19-nor-pregnahexaene-20-ones are prepared from the corresponding 19-nor-pregnapentaene-20-ones of this invention by reaction with a molar equivalent of 2,3-dichloro-5,6-dicycanobenzoquinone (DDQ) in an aprotic solvent (usually dioxane) in an essentially neutral medium. Isolation of the novel 19-nor-pregnahexaene-20-one anti-mitotic agents is then effected by methods well known in the steroid art. When the foregoing reaction is carried out in the presence of at least a molar equivalent of hydrogen chloride and with about two molar equivalents of DDQ, there are formed 15-chloro-19-nor-pregnahexaene-20-ones, a novel class of compounds. Thus, for example, reaction of 16α-methyl-1,3,5(10),6,8-19-nor-pregnapentaene-3,17α,21-triol-20-one 21-acetate in dioxane with at least a molar equivalent of hydrogen chloride and with about two molar equivalents of DDQ yields 15-chloro-16α-methyl-1,3,5(10),6,8,14-19-nor-pregnahexaene-3,17α,21-triol-20-one 21-acetate, having anti-mitotic activity.

Many of the 11-unsubstituted-1,3,5(10),6,8-19-nor-pregnapentaene-20-ones of this invention are known in the art and are prepared by reaction of a 9α,11β-dichloro-1,4-pregnadiene-17α,21-diol-3,20-dione 21-alkanoate (e.g., 16α-methyl-9α,11β-dichloro-1,4-pregnadiene-17α,21-diol-3,20-dione 21-acetate) with a weak base. preferably in the presence of lithium chloride. Weak bases useful in this process may be pyridine, collidine, lutidine and, preferably, dimethylformamide. Other 11-unsubstituted-19-nor-pregnapentaene-20-ones of our invention are also prepared from the corresponding 9α,11β-dichloro-1,4-pregnadiene-3,20-diones in similar manner.

Alternatively, the 11-unsubstituted-3-hydroxy-1,3,5(10),6,8-19-nor-pregnapentaene-20-ones of formula I are conveniently prepared from the corresponding 1,4,6,9(11)-pregnatetraene-3,20-diones by reaction with a nucleophilic acid (e.g., hydrochloric or hydrobromic acid) in an aprotic solvent (e.g., dioxane) whereby is formed a mixture of a 3-hydroxy-1,3,5(10),6,8-19-nor-pregnapentaene-20-one and the 3-methyl ether thereof which is isolated and separated via chromatographic techniques.

The 9α,11β-dichloro-1,4-pregnadiene-17α,21-diol-3,20-dione precursors to the 1,3,5(10),6,8-19-nor-pregnapentaene-20-ones of this invention are also known in the art, being prepared from the corresponding 9(11)-dehydro derivatives according to procedures such as described in U.S. Pat. Nos. 2,894,963 and 3,009,933.

Of the 11-oxygenated-19-nor-pregnapentaenes of this invention, described in the art is 11β-hydroxy-1,3,5(10),6,8-19-nor-pregnapentaene-3,17α,21-triol-21-acetate and its preparation from 9α-bromo-1,4,6-pregnatriene-11β,17α,21-triol-3,20-dione 21-acetate by reaction with pyridine at reflux temperature. Similar treatment with pyridine of other 9α-bromo-11β-hyroxy-1,4,6-pregnatriene derivatives, e.g., 9α-bromo-16α-methyl-1,4,6-pregnatriene-11β,17α,21-triol-3,20-dione 21-acetate will produce other 11β-hydroxy-19-nor-pregnapentaenes, e.g. 16α-methyl-1,3,5(10),6,8-19-nor-pregnapentaene-3,11β,17α,21-tetrol-20-one 21-acetate.

11-Oxo-19-nor-pregnapentaene compounds can be prepared from a 9α-bromo-11-oxo-1,4-pregnadiene when subjected to enol benzoylating conditions. Thus, for example, 9α-bromo-16α-methyl-1,4-pregnadiene-17α,21-diol-3,11,20-trione 21-acetate, upon reaction with benzoyl chloride in pyridine yields 16α-methyl-1,3,5(10),6,8-19-nor-pregnapentaene-3,17α,21-triol-11,20-dione 21-acetate.

Alternatively, both 11-oxo and 11β-hydroxy-19-nor-pregnapentaene compounds may be prepared from the corresponding 3-oxo-1,4,6,8-pregnatetraene by treatment thereof under aromatizing conditions such as by reaction in tetrahydrofuran in the presence of acid or by reaction with lithium chloride in dimethylformamide in the presence of acid. Thus, for example, treatment of 16β-methyl-1,4,6,8-pregnatetraene-11β,17α,21-triol-3,20-dione 21-acetate in tetrahydrofuran with hydrochloric acid yields an 11-hydroxy-19-nor-pregnapentaene compound of this invention, e.g., 16β-methyl-1,3,5(10),6,8-19-nor-pregnapentaene-3,11β,17α,21-tetrol-20-one 21-acetate. The requisite 3-oxo-11-oxygenated-1,4,6,8-pregnatetraenes are, in turn, derived from the corresponding 3-oxo-9α-halogeno-1,4,6-pregnatiene by treatment with base. For example, 9α-chloro-16β-methyl-1,4,6-pregnatriene-11β,17α,21-triol-3,20-dione 21-acetate, upon reaction with potassium acetate in methanol yields 16β-methyl-1,4,6,8-pregnatetraene-11β,17α,21-triol-3,20-dione 21-acetate. If desired, when carrying out the foregoing dehydrohalogenation at C-8,9 when introduction of a double bond at C-8, one can simultaneously oxidize an 11β-hydroxy group to an 11-oxo function according to known procedures. Thus, treatment of 9α-bromo-11β-hydroxy-1,4,6-pregnatriene-17α,21-diol-3,20-dione 21-acetate in pyridine with chromic acid yields 11-oxo-1,4,6,8-pregnatetraene-17α,21-diol-3,20-dione 21-acetate. Alternatively, a 1,4,6,8-pregnatetraene-11β,17α,21-triol-3,20-dione may be oxidized to the corresponding 11-oxo derivative with maganeses dioxide.

When preparing 11-hydroxy-1,3,5(10),6,8,14-19-nor-pregnahexaenes of formula I, one may reduce the corresponding 11-oxo-19-nor-pregnahexaene of formula I by means of agents known to reduce oxo functions to hydroxyl, such as with sodium borohydride. When carrying out this reaction, it is necessary to block the 20-oxo function in the dihydroxy acetone side chain at C-17 so that the 20-oxo will not be reduced. Portection of the 20-oxo may be effected via known methods such as by preparing a 17α,20;20,21-bismethylenedioxy derivative or by preparing a 17,21-diester. When reducing an 11-oxo-19-nor-pregnapentaene of formula I to the corresponding 11-hydroxy-19-nor-pregnapentaene, there is usually obtained a mixture of the 11α-hydroxy and 11β-hydroxy epimers which are separable by chromatographic techniques. Thus, for example, treatment of 16α-methyl-1,3,5(10),6,8-19-nor-pregnapentaene-3,17α,21-triol-11,20-dione 3,17,21-tripropionate with sodium borohydride yields a mixture of the corresponding 11α-and 11β-hydroxy derivatives together with the corresponding 3,11β-dihydroxy derivatives which, after separation via chromatography over silica gel and hydrolysis of the ester functions by means of methanolic sodium bicarbonate, yields 16α-methyl-1,3,5(10),6,8-19-nor-pregnapentaene-3,11β,17α,21-tetrol-20-one and the corresponding 11α-hydroxy derivative of formula I, respectively.

When preparing a 16-alkylidene compound of formula I (i.e. a compound wherein W is =CHT), one may start with a 9α,11β-dichloro-16-alkylidene-1,4-pregnadiene-17α,21-diol-3,20-dione 21-lower alkanoate precursor and convert it to a 16-alkylidene-1,3,5(10),6,8-19-nor-pregnapentaene according to the process described hereinabove.

Alternatively, to minimize side reactions which occur when halogenating a 9(11)-dehydro-16-methylene-17α-hydroxy-1,4-pregnadiene-3,20-dione, one may protect the 17α-hydroxyl function thereof such as by a 17α,21-alkylidenedioxy derivative before or after introduction of the 9(11)-double bond prior to preparing the corresponding 9α,11β-dichloro derivative of the 17α-hydroxy protected derivative of a 16-methylene-1,4,9(11)-pregnatriene-3,20-dione (e.g. 16-methylene-9α,11β-dichloro-1,4-pregnadiene-17α,21-diol-3,20-dione 17,21-acetonide). After conversion thereof to a 16-alkylidene-1,3,5(10),6,8-19-nor-pregnapentaene-3-ol of formula I (e.g. 16-methylene-1,3,5(10),6,8-19-nor-pregnapentaene-3,17α,21-triol-20-one 17,21-acetonide), the 17α-hydroxy protecting groups may be easily removed via known techniques (e.g. by means of aqueous acetic acid) to obtain a 16-alkylidene-1,3,5(10),6,8-19-nor-pregnapentaene-3,17α,21-triol-20-one of this invention (e.g. 16-methylene-1,3,5(10),6,8-19-nor-pregnapentaene-3,17α,21-triol-20-one).

In general, when a 21-mono-lower alkanoate or a 17,21-dilower alkanoate derivative of a 3-hydroxy-19-nor-pregnapentaene-20-one of formula I is desired, it is preferable to use as starting compound a 9α,11β-dichloro-1,4-pregnadiene-17α,21-diol-3,20-dione precursor containing the desired 21-mono-alkanoate or 17,21-dialkanoate ester function prior to reaction with a weak base to produce a 1,3,5(10),6,8-19-nor-pregnapentaene-3,17α,21-triol-20-one 17-mono- or 17,21-dialkanoate anti-mitotic agent of this invention.

A 17-mono-lower alkanoate ester derivative of a 3-hydroxy-19-nor-pregnapentaene-20-one of formula I may be prepared by reaction of an unesterified precursor (e.g. 16α-methyl-1,3,5(10),6,8-19-nor-pregnapentaene-3,17α,21-triol-20-one) in an aprotic solvent (e.g. dimethylsulfoxide) with at least one molar equivalent of a trilower alkyl ortho ester (e.g. triethylorthopropionate) in the presence of a strong acid (e.g. p-toluenesulfonic acid) followed by hydrolytic cleavage of the resulting 17α,21-ortho ester by means of aqueous acid (e.g. aqueous acetic acid), thence separation and isolation of the 17-mono-ester using known techniques, usually including chromatographic methods, whereby is obtained a 17-mono-alkanoate (e.g. the 17-propionate). By this procedure, there is usually also produced some of the corresponding 21-mono-alkanoate derivatives (e.g. the 21-propionate) which may also be isolated via chromatographic techniques.

A 3,17α-diester derivative of formula I is conveniently derived from a 3-hydroxy-17α,21-orthoester intermediate (prepared as described hereinabove) by reaction thereof with an acid anhydride or acid halide in pyridine (e.g. acetic anhydride in pyridine) to form the corresponding 3-alkanoate 17α,21-orthoester intermediate which, after hydrolytic cleavage of the 17α,21-orthoester group by means of aqueous acetic acid, yields a 3,17-diester of formula I.

The 3,21-diester derivatives are conveniently prepared from the corresponding 21-monoester; the 3,17α,21-triesters may be prepared from the corresponding 3,17α,21-triol or 17α,21- or 3,17α-diesters utilizing conventional esterification techniques.

To prepare a 3-monoester derivative of formula I, it is necessary to protect the 21-hydroxyl group (e.g., by an ether derivative such as the 21-methoxyethoxymethyl ether) in the 9α,11β-dichloro-1,4-pregnadiene-20-one precursor (e.g., by reaction of 16α-methyl-9α,11β-dichloro-1,4-pregnadiene-17α,21-diol-3,20-dione with triethylmethoxyethoxymethylammonium chloride in acetonitrile) prior to reaction thereof with a weak base in the presence of lithium chloride to produce the corresponding 3-hydroxy-1,3,5(10),6,8-19-nor-pregnapentaene-20-one (e.g. 16α-methyl-1,3,5(10),6,8-19-nor-pregnapentaene-3,17α,21-triol-20-one 21-methoxyethoxymethyl ether). Treatment of the 21-protected-1,3,5(10),6,8-19-nor-pregnapentaene 20-one according to standard esterification procedures (e.g. by reaction with acetic anhydride in pyridine), yields the corresponding 3-monoester 21-methoxyethoxymethyl ether derivative. Upon cleavage of the 21-ether function, e.g. by means of zinc bromide in methylene chloride, there is then produced a 3-monoester of formula I (e.g. 16α-methyl-1,3,5(10),6,8,19-nor-pregnapentaene-3,17α,21-triol-20-one 3-acetate).

The 3-alkoxy derivatives of formula I are prepared via known esterification techniques such as those utilizing a diazoalkane (e.g. diazomethane in ether). Thus, a 3-alkoxy 21-ester or a 3-alkoxy 17,21-diester derivative is prepared from the corresponding 3-hydroxy 21-ester or 3-hydroxy 17,21-diester derivatives by reaction with a diazoalkane in ether.

A derivative of formula I having a 3-alkoxy group and hydroxyl functions at 17 and 21 may be conveniently derived from a 3-alkoxy 21-ester derivative via hydrolysis such as with aqueous sodium bicarbonate in methanol.

In order to prepare a 3-alkoxy 17-ester derivative of a compound of formula I (e.g. 16α-methyl-1,3,5(10),6,8-19-nor-pregnapentaene-3,17α,21-triol-20-one 17-acetate 3-methyl ether), it is preferable to first prepare a 17α,21-orthoester derivative of a 3,17α,21-triol of formula I according to procedures described hereinabove followed by reaction thereof with a diazoalkane (e.g. diazomethane) to produce a 3-alkoxy-17α,21-orthoester derivative followed by cleavage of the 17α,21-orthoester by means of dilute acid to obtain a 3-alkoxy 17-ester derivative of formula I.

When preparing a 16α,17α-alkylidenedioxy derivative of formula I, the 16α,17α-alkylidenedioxy function may be introduced into the molecule prior to or after preparation of the corresponding 16α,17α-dihydroxy-1,3,5(10),6,8,19-nor-pregnapentaene-20-one; however, a 17α,21-alkylidenedioxy derivative of formula I is usually introduced after preparation of the corresponding 17α,21-dihydroxy-1,3,5(10),6,8,19-nor-pregnapentaene-20-one. Both the 16α,17α- or 17α,21-alkylidenedioxy derivatives of the 1,3,5(10),6,8,-19-nor-pregnapentaene-20-ones of formula I are prepared from the corresponding 16α,17α-dihydroxy- or 17α,21-dihydroxy- steroid upon reaction with a ketone or aldehyde (e.g. acetone, acetaldehyde, acetophenone) in the presence of a mineral acid (e.g. hydrochloric acid).

The 17α,20;20,21-bismethylenedioxy function can be introduced prior to or after introduction of the 19-nor-pregnapentaene system by known reactions such as that utilizing formaldehyde in the presence of acid.

THE METHOD-OF-USE AND PHARMACEUTICAL FORMULATION ASPECT OF THE INVENTION

The method-of-use aspect of this invention resides in the concept of the method of eliciting a mitotic inhibitory response in a warm-blooded animal having a disease characterized by rapid cell proliferation which comprises administering to said animal a non-toxic, mitotic inhibitory effective amount of a 19-nor-pregnapentaene-20-one of formula I defined hereinabove, together with a non-toxic, pharmaceutically acceptable carrier.

Our method is particularly useful in the treatment and control of proliferative skin diseases, and is primarily useful for the treatment of psoriasis via the topical route.

Psoriasis is characterized by increased epidermipoiesis associated with a high mitotic rate, rapid cell turnover and altered keratinization. The psoriatic epidermis can be normalized by slowing down cell growth through inhibiting mitosis.

All drugs currently used in psoriasis therapy are known to directly or indirectly reduce epidermal mitotic activity. Although there is no animal model for psoriasis, many of these same drugs have been reported to have a similar effect in models of epidermal hyperplasia which simulate psoriasis in laboratory animals.

Topically effective anti-psoriatic drugs, including corticosteroids, anthralin, coal tar and 5-fluorouracil, while relatively free of systemic side effects, cause local adverse reactions. Thus, corticosteroid therapy causes skin atrophy, telangiectasia and the formation of striae, while anthralin and 5-fluorouracil are skin irritants and require close clinical supervision for optimal therapeutic benefit. Anthralin can also cause staining of the skin.

By our invention, we have discovered that 1,3,5(10),6,8,-19-nor-pregnapentaene-3,17α,21-triol-20-one and derivatives thereof (particularly 1,3,5(10),6,8-19-nor-pregnapentaene-3,17α,21-triol-20-one 21-acetate and 16-methyl homologs thereof reduce epidermal mitotic activity without causing significant local or systemic hormonal or toxic effects when applied topically to the skin of mice in which epidermal mitosis has been stimulated.

Specifically, when treated by a procedure modified from S. Belman and W. Troll, Cancer Research 32:450–454 (1972), the 19-nor-pregnapentaene-20-ones of this invention, particularly the derivatives of formula II, reduce croton-oil stimulated epidermal mitosis in mice when applied topically. Moreover, the 19-nor-pregnapentaene-20-ones are non-irritating without causing hormonal side effects which is surprising in view of the structure of the 19-nor-pregnapentaene-20-ones which has an aromatic A ring such as in many estrogens, and a corticoid side chain as in potent topical anti-inflammatory agents such as dexamethasone 17-valerate and betamethasone dipropionate.

In the foregoing test, croton-oil is applied topically to shaved mice, thus accelerating mitosis. A 1,3,5(10),6,8,19-nor-pregnapentaene-3,17α,21-triol-20-one of this invention is applied topically to the stimulated site, then 24 hours later portions of the treated skin are excised for histologic processing, mitotic figures per thousand basal interfollicular epidermal cells being counted in a light microscope. Epidermal mitotic counts from drug-treated mice are compared to counts from lesion controls for statistically signficant differences with an analysis of variance. The mitotic count for each compound tested is expressed as percent reduction of mitoses compared with the number of mitoses on the skin of mice treated with croton-oil alone. In general, it was discovered that the 19-nor-pregnapentaene-20-ones of this invention such as are defined by formula I reduce croton-oil stimulated epidermal mitosis.

The 19-nor-pregnapentaene-20-ones of this invention, particularly 1,3,5(10),6,8-19-nor-pregnapentaene-3,17α,21-triol-20-one 21-acetate, the 16-methyl homologs thereof and the corresponding 11-oxo derivatives are also contemplated as exhibiting anti-mitotic activity when administered orally or parenterally to mice without causing significant local or systemic hormonal or toxic effects.

In view of the anti-mitotic and anti-acanthotic activity of the 19-nor-pregnapentaene-20-ones of this invention, when applied topically, our invention includes the concept of the method of treating and controlling psoriasis which comprises applying topically to the affected area in a concentration effective for the treatment of psoriasis, a 19-nor-pregnapentaene-20-one of formula I together with a non-toxic, pharmaceutically acceptable carrier. Preferred anti-psoriatic agents of this invention are the 19-norpregnapentaene-20-ones of formula II, particularly 16α-methyl-1,3,5(10),6,8-19-nor-pregnapentaene-3,17α,21-triol-20-one 21-acetate and the 16α-methyl and 16β-methyl homologs thereof.

Included within the term "topically applying" are topical applications on skin whereby our compounds are effective in the treatment and control of skin diseases characterized by rapid cell proliferation and/or abnormal cell proliferation, e.g. psoriasis; aerosol application; and subcutaneous injection application whereby our compounds are effective in the treatment of local epidermal disorders.

When carrying out a preferred mode of our method, a pharmaceutical formulation comprising a 19-nor-pregnapentaene-20-one of formula I, preferably a compound of formula II such as 1,3,5(10),6,8-19-nor-pregnapentaene-3,17α,21-triol-20-one 21-acetate, together with a non-toxic, pharmaceutically acceptable carrier, usually in concentrations in the range of from about 0.0001 percent to about 5 percent, preferably from about 0.1 percent to about one percent, is applied several times daily to skin affected by psoriasis until the psoriatic condition has improved. Topical applications of the 19-nor-pregnapentaene-20-one may then be continued at less frequent intervals (e.g. once a day) to control mitoses in order to prevent return of severe psoriatic conditions.

The 19-nor-pregnapentaene-20-ones of formula I and, preferably, formula II, are conveniently applied in a liquid solvent, preferably in a water-miscible liquid carrier made up of hydrophylic liquids having a high solvating action, e.g. a solution of 1,3,5(10),6,8-19-nor-pregnapentaene-3,17α,21-triol-20-one 21-acetate together with polyethylene glycol. In general, the 19-nor-pregnapentaene-20-ones may be applied in any topical form including creams, lotions, aerosols and ointments, which are prepared by combining the ingredient, e.g. a 19-nor-pregnapentaenes such as defined by formula I, with conventional pharmaceutical diluents and carriers used in topical formulations comprising steroids.

Thus, the pharmaceutical formulation aspect of this invention resides in the concept of a pharmaceutical composition, for the treatment of psoriasis, preferably for topical application, comprising an anti-psoriatic effective amount of a 19-nor-pregnapentaene-20-one of formula I together with a non-toxic, pharmaceutically acceptable carrier.

Preferred are topical formulations comprising 19-nor-pregnapentaene-20-ones of formula II.

The pharmaceutical formulations are made according to known procedures, some of which are described in detail in the Examples hereinbelow. Typical formulations include ointments, lotions, creams, sprays, powders, drops, (e.g. ear drops), suppositories, and aerosols. Ointments and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, polyethylene glycols, woolfat, hydrogenated lanolin, beeswax, etc.

Lotions may be formulated with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g. talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g. methyl hydroxybenzoate, propyl hydroxybenzoate, chlorocresol, benzalkonium chlorides, etc.

The compositions according to the invention may also contain other active ingredients such as antimicrobial agents, particularly antibiotics.

In addition to the topical pharmaceutical compositions of the invention described in detail hereinabove and in the formulations below, our inventive concept includes pharmaceutical formulations for administration orally or parenterally, made according to standard procedures and comprising an anti-mitotic amount of a 1,3,5(10),6,8-19-nor-pregnapentaene-20-one of formula I together with a non-toxic, pharmaceutically acceptable carrier.

The proportion of active steroid in the topical compositions according to the invention depends on the precise type of formulations to be prepared but will generally be within the range of from 0.0001% to 5% by weight. Generally, however, for most types of topical preparations the proportion of active steroid used will be within the range of from 0.1 to 3% and preferably 0.1% to 1%.

The following formulations exemplify some of the dosage forms in which the anti-mitotic agents of our invention may be employed. In each, the active ingredient is 1,3,5(10),6,8-19-nor-pregnapentaene-3,17α,21-triol-20-one 21-acetate. It is understood, however, that this compound may be replaced by equivalent quantities of other active 19-nor-pregnapentaenes of this invention, e.g. the 16α-methyl or 16β-methyl homologs of 1,3,5(10),6,8,-19-nor-pregnapentaene-3,17α,21-triol-20-one or of the 21-acetate ester thereof or the corresponding 11-oxo or 11-hydroxy derivatives of the foregoing.

FORMULATIONS

| Formulation I: Ointment | |
|---|---|
| Formula | mg/g |
| 1,3,5(10),6,8-19-nor-pregna-pentaene-3,17α,21-triol-20-one 21-acetate, Micronized | 1.0–20.0 |
| Benzyl Alcohol, NF | 10.0 |
| Mineral Oil, USP | 50.0 |
| White Petrolatum, USP to make | 1.0 g |

Procedure

Mix and heat to 65° C. a weighed quantity of white petrolatum, mineral oil, benzyl alcohol, and cool to 50°–55° C. with stirring. Disperse 1,3,5(10),6,8-19-nor-pregnapentaene-3,17α,21-triol-20-one 21-acetate in a portion of the mineral oil and then add to the above mixture with stirring. Cool to room temperature.

| Formulation II: Cream | |
|---|---|
| Formula | mg/g |
| 1,3,5(10),6,8-19-nor-pregna-pentaene-3,17α,21-triol-20-one 21-acetate | 1.0–20.0 |
| Stearic Acid, USP | 60.0 |
| Glyceryl Monostearate, Cosmetic | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Procedure

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed lightning stirring. Dissolve the 1,3,5(10),6,8-19-nor-pregnapentaene-3,17α,21-triol-20-one 21-acetate in remaining quantity of propylene glycol and add to the above emulsion when the temperature of emulsion is 37°–40° C. Mix uniformly with stirring and cool to room temperature.

| Formulation III: Gel | |
|---|---|
| Formula | mg/g |
| 1,3,5(10),6,8-19-nor-pregna-pentaene-3,17α,21-triol-20-one 21-acetate | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | 669.3–688.3 |

Procedure

Prepare a 1% solution of the sodium hydroxide in propylene glycol and hold. Add approximately one-half the remaining propylene glycol, and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and recirculation until a thick gel forms. Dissolve the 1,3,5(10),6,8-19-nor-pregnapentaene-3,17α,21-triol-20-one 21-acetate in the remaining propylene glycol and add to the gel slowly as the gel is continuously recirculated.

| Formulation IV: Lotion | |
|---|---|
| Formula | mg/g |
| 1,3,5(10),6,8-19-nor-pregna-pentaene-3,17α,21-triol-20-one 21-acetate | 1.0–20.0 |
| Carbomer 940 (G.W. Goodrich) | 3.0 |
| Sodium hydroxide (charged as 4% w/w aqueous solution) | 0.05 |
| Isopropyl Alcohol | 40.00 |
| Purified Water, USP to make | 1.0 g |

Procedure

Prepare a 4% solution of sodium hydroxide in water. Heat the purified water to 60° C. Add carbomer 940 and mix at high speed until dispersed. Cool the above mixture to room temperature and slowly charge sodium hydroxide solution until uniform. Add 80% of isopropyl alcohol to the above with mixing. Dissolve 1,3,5(10),6,8-19-nor-pregnapentaene-3,17α,21-triol-20-one 21-acetate in remaining isopropanol. Add this to the mixture with stirring. Adjust pH to 5.0 to 5.5 with sodium hydroxide, if necessary.

Formulation V: Tablet

| Formula | 10 mg. Tab. | 25 mg. Tab. | 100 mg. Tab. |
|---|---|---|---|
| 1,3,5(10),6,8-19-nor-pregnapenta-ene-3,17α,21-triol-20-one 21-acetate | 10.5* mg. | 26.25* mg. | 105.0* mg. |
| Lactose, impalpable powder | 197.50 mg. | 171.25 mg. | 126.00 mg. |
| Corn Starch | 25.00 mg | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |
| *5% excess | | | |

Procedure

Prepare a slurry consisting of 1,3,5(10),6,8-19-nor-pregnapentaene-3,17α,21-triol-20-one 21-acetate, lactose and polyvinylpyrrolidone. Spray dry the slurry.

Add the corn starch and magnesium stearate. Mix and compress into tablets.

EXAMPLE 1

16α-Methyl-1,3,5(10),6,8-19-Nor-Pregnapentaene-3,17α,21-Triol-20-One 21-Acetate

To a refluxing solution of lithium chloride (120 gms.) and concentrated hydrochloric acid (1.8 ml.) in dimethylformamide (750 ml.) add 9α,11β-dichloro-16α-methyl-1,4-pregnadiene-17α,21-diol-3,20-dione 21-acetate (30 gms.). Heat the reaction mixture at reflux temperature for 15 minutes, then pour into water/ice (6 liters). Extract the aqueous mixture with ethyl acetate, wash the combined extracts with water, then evaporate to a volume of about 350 ml. Separate the resultant crystalline precipitate by filtration, wash the precipitate with ethyl acetate and air dry to obtain 16α-methyl-1,3,5(10),6,8-19-nor-pregnapentaene-3,17α,21-triol-20-one 21-acetate (yield=9.6 gms.); m.p. 235°–240° C., $[\alpha]_D^{26}$ +101° (dioxane), $\lambda_{max}^{methanol}$ 230 ($\epsilon$=81,100), 258 ($\epsilon$=3,600), 269 ($\epsilon$=4,900), 280 ($\epsilon$=5,600), 292 ($\epsilon$=4,100), 326 ($\epsilon$=2,400), 346 nm ($\epsilon$=800).

EXAMPLE 2

Other 1,3,5(10),6,8-19-Nor-Pregnapentaene-3,17α,21-Triol-20-Ones

In a manner similar to that described in Example 1A, treat each of the following 9α,11β-dihalogeno-1,4-pregnadienes with lithium chloride in dimethylformamide.
(1) 9α,11β-dichloro-16β-methyl-1,4-pregnadiene-17α,21-diol-3,20-dione 21-acetate,
(2) 9α,11β-dichloro-16α-methyl-1,4-pregnadiene-17α,21-diol-3,20-dione 17,21-di-n-butyrate,
(3) 9α,11β-dichloro-1,4-pregnadiene-17α,21-diol-3,20-dione 21-acetate,
(4) 6α,16α-dimethyl-9α,11β-dichloro-1,4-pregnadiene-17α,21-diol-3,20-dione 21-acetate,
(5) 6α-methyl-9α,11β-dichloro-1,4-pregnadiene-17α,21-diol-3,20-dione 21-acetate,
(6) 6α-fluoro-9α,11β-dichloro-1,4-pregnadiene-17α,21-diol-3,20-dione 21-acetate,
(7) 6α-fluoromethyl-9α,11β-dichloro-1,4-pregnadiene-17α,21-diol-3,20-dione 21-acetate,
(8) 6α-difluoromethyl-9α,11β-dichloro-1,4-pregnadiene-17α,21-diol-3,20-dione 21-acetate,
(9) 6α-trifluoromethyl-9α,11β-dichloro-1,4-pregnadiene-17α,21-diol-3,20-dione 21-acetate,
(10) 9α,11β-dichloro-1,4-pregnadiene-16α,17α,21-triol-3,20-dione 16,21-diacetate,
(11) 9α,11β-dichloro-16α,17α-isopropylidenedioxy-1,4-pregnadien-21-ol-3,20-dione 21-acetate,
(12) 6α,16β-dimethyl-9α,11β-dichloro-1,4-pregnadiene-17α,21-diol-3,20-dione 21-acetate.

Isolate and purify each of the resultant products in a manner similar to that described in Example 1A to obtain, respectively,
(1) 16β-methyl-1,3,5(10),6,8-19-nor-pregnapentaene-3,17α,21-triol-20-one 21-acetate, m.p. 182°–184° C., $[\alpha]_D^{26}$ +122° (chloroform), $\lambda_{max}^{methanol}$ 229 ($\epsilon$=67,000), 258 ($\epsilon$=3,700), 268 ($\epsilon$=4,800), 279 ($\epsilon$=5,500), 291 ($\epsilon$=4,000), 327 ($\epsilon$=2,400), 340 nm ($\epsilon$=2,700),
(2) 16α-methyl-1,3,5(10),6,8-19-nor-pregnapentaene-3,17α,21-triol-20-one 17,21-di-n-butyrate, m.p. 200°–202° C., $[\alpha]_D^{26}$ −15° (dioxane), $\lambda_{max}^{methanol}$ 228 ($\epsilon$=67,000), 257 ($\epsilon$=4,000), 268 ($\epsilon$=5,100), 279 ($\epsilon$=5,700), 290 ($\epsilon$=4,000), 325 ($\epsilon$=2,300), 340 nm ($\epsilon$=2,700),
(3) 1,3,5(10),6,8-19-nor-pregnapentaene-3,17α,21-triol-20-one 21-acetate, m.p. 185°–190° C., $[\alpha]_D^{26}$ +91° (chloroform), $\lambda_{max}^{methanol}$ 229 (E=66,400), 258 ($\epsilon$=3,600), 268 ($\epsilon$=4,900), 281 ($\epsilon$=5,700), 291 ($\epsilon$=4,200), 327 ($\epsilon$=2,600), 340 nm ($\epsilon$=3,100),
(4) 6,16α-dimethyl-1,3,5(10),6,8-19-nor-pregnapentaene-3,17α,21-triol-20-one 21-acetate,
(5) 6-methyl-1,3,5(10),6,8-19-nor-pregnapentaene-3,17α,21-triol-20-one 21-acetate,
(6) 6-fluoro-1,3,5(10),6,8-19-nor-pregnapentaene-3,17α,21-triol-20-one 21-acetate,
(7) 6-fluoromethyl-1,3,5(10),6,8-19-nor-pregnapentaene-3,17α,21-triol-20-one 21-acetate,
(8) 6-difluoromethyl-1,3,5(10),6,8-19-nor-pregnapentaene-3,17α,21-triol-20-one 21-acetate,
(9) 6-trifluoromethyl-1,3,5(10),6,8-19-nor-pregnapentaene-3,17α,21-triol-20-one 21-acetate,
(10) 1,3,5(10),6,8-19-nor-pregnapentaene-3,16α,17α,21-tetrol-20-one 16,21-diacetate,
(11) 16α,17α-isopropylidenedioxy-1,3,5(10),6,8-19-nor-pregnapentaene-3,21-diol-20-one 21-acetate,
(12) 6,16β-dimethyl-1,3,5(10),6,8-19-nor-pregnapentaene-3,17α,21-triol-20-one 21-acetate.

EXAMPLE 3

1,3,5(10),6,8-19-Nor-Pregnapentaene-3,17α,21-Triol-20-One and Derivatives Thereof

A.

16α-Methyl-1,3,5(10),6,8-19-Nor-Pregnapentaene-3,17α,21-Triol-20-One

To a solution of 16α-methyl-1,3,5(10),6,8-19-nor-pregnapentaene-3,17α,21-triol-20-one 21-acetate (1 gm.) in methanol (70 ml.) under an atmosphere of nitrogen, with aqueous sodium bicarbonate (10%, 5 ml.). Heat at reflux temperature for 30 minutes, cool, add dilute acetic acid until the reaction mixture is at about pH 7, pour into water and extract with ethyl acetate. Wash the combined extracts with water, dry over magnesium sulfate and evaporate. Crystallize the resultant residue from chloroform:ethyl acetate to obtain 16α-methyl-1,3,5(10),6,8-19-nor-pregnapentaene-3,17α,21-triol-20-one.

B. In similar manner, treat each of the esterified products prepared in Example 2 with aqueous sodium bicarbonate in methanol and isolate and purify each of the resultant products in the described manner to obtain the corresponding 1,3,5(10),6,8-19-nor-pregnapentaene-3,17α,21-triol-20-one free of ester groups.

EXAMPLE 4

3-Alkoxy-1,3,5(10),6,8-19-Nor-Pregnapentaene-17α,21-Diol-20-Ones

A.

3-Methoxy-16α-Methyl-1,3,5(10),6,8-19-Nor-Pregnapentaene-17α,21-Diol-20-One 21-Acetate To a suspension of 16α-methyl-1,3,5(10),6,8-19-nor-pregnapentaene-3,17α,21-triol-20-one 21-acetate (1 gm.) in dioxane (50 ml.) add a solution of diazomethane in ether, (molar quantity of diazomethane being in excess of the pregnapentaene). Allow the reaction mixture to stand at room temperature overnight, then distill the excess diazomethane. Purify the resultant residue via chromatography on silica gel preparative plates using as solvent system chloroform:ethyl acetate (4:1). Remove the band containing the desired product as visualized under ultraviolet light by extraction with ethyl acetate. Evaporate the ethyl acetate solution and crystallize the resultant residue from petroleum ether/ether to obtain 3-methoxy-16α-methyl-1,3,5(10),6,8-19-nor-pregnapentaene-17α,21-diol-20-one 21-acetate.

B. In similar manner, treat each of the 3-hydroxy-1,3,5(10),6,8-19-nor-pregnapentaenes of Example 2 with diazomethane to obtain the corresponding 3-methyl ethers thereof.

C. In the procedures of Examples 3A and 3B, by substituting for diazomethane other diazoalkane solutions, e.g. diazoethane, there is obtained the corresponding 3-alkoxy derivatives, e.g. the 3-ethoxy derivatives, corresponding to the 3-methoxy products of Examples 3A and 3B.

EXAMPLE 5

Preparation of 3-Hydrocarboncarboxylate Esters

A.

16α-Methyl-1,3,5(10),6,8-19-Nor-Pregnapentaene-3,17α,21-Triol-20-One 3,21-Diacetate To a solution of 16α-methyl-1,3,5(10),6,8-19-nor-pregnapentaene-20-one 21-acetate (450 mg.) in pyridine (2 ml.), add acetic acid (1 ml.) and allow the reaction mixture to stand at room temperature overnight. Pour the reaction mixture into dilute hydrochloric acid, separate the resultant precipitate by filtration, wash the precipitate with water, dry and crystallize from ether to obtain 16α-methyl-1,3,5(10),6,8-19-nor-pregnapentaene-3,17α,21-triol-20-one 3,21-diacetate.

B.

16α-Methyl-1,3,5(10),6,8-19-nor-Pregnapentaene-3,17α,21-Triol-20-one 3-Benzoate 21-Acetate To a solution of 16α-methyl-1,3,5(10),6,8-19-nor-pregnapentaene-3,17α,21-triol-20-one 21-acetate (1 gm.) in pyridine (20 ml.) add benzoyl chloride (1 ml.) and stir at room temperature overnight. Pour the reaction mixture into dilute aqueous hydrochloric acid and extract with ethyl acetate. Wash the combined ethyl acetate extracts with water, aqueous sodium bicarbonate, then water, and concentrate the ethyl acetate extracts in vacuo to a low volume, cool, then separate the resultant crystalline by filtration to obtain 16α-methyl-1,3,5(10),6,8-19-nor-pregnapentaene-3,17α,21-triol-20-one 17-benzoate 21-acetate (yield = 1.03 gms.).

C. In similar manner, treat each of the 3-hydroxy-1,3,5(10),6,8-19-nor-pregnapentaene compounds prepared in Example 2 with acetic anhydride in pyridine or benzoyl chloride in pyridine to obtain the corresponding 3-acetate or 3-benzoate ester thereof, respectively.

EXAMPLE 6

Preparation of 17-Mono-Lower Alkanoate and 21-Mono-Lower Alkanoate From the Corresponding 1,3,5(10),6,8-19-Nor-Pregnapentaene-3,17α,21-Triol-20-One A. The 21-Propionate and 17-Propionate of 16α-Methyl-1,3,5(10),6,8-19-Nor-Pregnapentaene-3,17α,21-Triol-20-One To a solution of 16α-methyl-1,3,5(10),6,8-19-nor-pregnapentaene-3,17α,21-triol-20-one (697 mg.) in dimethylsulfoxide (9.7 ml.), add triethylorthopropionate (0.97 ml.) and p-toluenesulfonic acid (97 mg.). Stir at room temperature for 5 hours, then add acetic acid/water (14 ml., 9:1) and stir the mixture at room temperature overnight. Pour the reaction mixture into water and separate the resultant precipitate by filtration. Wash the precipitate with water, then chromatograph over silica gel eluting with methylene chloride:ether (19:1). Combine the like fractions containing the 17-mono-propionate ester and combine the like fractions containing the 21-mono-propionate ester as determined by thin layer chromatography. Evaporate each of the combined fractions to residues comprising 16α-methyl-1,3,5(10),6,8-19-nor-pregnapentaene-3,17α,21-triol-20-one 21-propionate and 16α-methyl-1,3,5(10),6,8-19-nor-pregnapentaene-3,17α,21-triol-20-one 17-propionate, respectively.

B. In similar manner, treat each of 16β-methyl-1,3,5(10),6,8-19-nor-pregnapentaene-3,17α,21-triol-20-one and 1,3,5(10),6,8-19-nor-pregnapentaene-3,17α,21-triol-20-one with triethylorthopropionate in p-toluenesulfonic acid followed by treatment with aqueous acetic acid. Isolate and purify each of the resulting products in a manner similar to that described to obtain 16β-methyl-1,3,5(10),6,8-19-nor-pregnapentaene-3,17α,21-triol-20-one 21-propionate and 16β-methyl-1,3,5(10),6,8-19-nor-pregnapentaene-3,17α,21-triol-20-one 17-propionate; 1,3,5(10),6,8-19-nor-pregnapentaene-3,17α,21-triol-20-one 21-propionate and 1,3,5(10),6,8-19-nor-pregnapentaene-3,17α,21-triol-20-one 17-propionate.

EXAMPLE 7

Alternate Procedure for the Preparation of 1,3,5(10),6,8-19-Nor-Pregnapentaene-17α,21-Diol-3,20-Dione 21-Acetate and the 3-Methyl Ether Thereof A. 1,4,6,9(11)-Pregnatetraene-17α,21-Diol-3,20-Dione 21-Acetate To a solution of 1,4,6-pregnatriene-11β,17α,21-triol-3,20-dione 21-acetate (1 gm.) in dimethylformamide (6 ml.) and s-collidine (2 ml.), add a 3.5% solution of sulfur dioxide in methanesulfonyl chloride (w/v) (0.6 ml.) at 0° C. Stir the reaction mixture at 0° C. for 30 minutes, and then at room temperature for 2 hours. Pour into water, separate the resultant precipitate by filtration, then wash the precipitate with water, air dry, and purify by crystallization from ethyl acetate/hexane to give 1,4,6,9(11)-pregnatetraene-17α,21-diol-3,20-dione 21-acetate (yield = 0.5 gms.).

B.

1,3,5(10),6,8-19-Nor-Pregnapentaene-3,17α,21-Triol-20-One 21-Acetate and the 3-Methyl Ether Thereof To a solution of dry halogen chloride (3.33 gms.) in dioxane (100 ml.), add 1,4,6,9(11)-pregnatetraene-17α,21-diol-3,20-dione 21-acetate (2.5 gms.) and stir at room temperature for 18 hours. Evaporate the reaction mixture in vacuo at room temperature and chromatograph the resultant residue on a column of silica gel (250 gms.) eluting with chloroform/ethyl acetate (17:3). Combine the early, like fractions containing 3-methoxy-1,3,5(10),6,8-19-nor-pregnapentaene-17α,21-diol-20-one 21-acetate as determined by thin layer chromatography, evaporate the combined fractions to a residue, and crystallize from methanol to obtain 3-methoxy-1,3,5(10),6,8-19-nor-pregnapentaene-17α,21-diol-20-one 21-acetate; nmr (dmso-d$_6$) δ 0.42 (C$_{13}$-CH$_3$);

2.10 (OCCH$_3$) 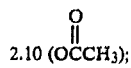;

3.85 (3-O-CH$_3$); 5.06 (C$_{21}$-H); 7.0–8.0 (Aromatic H's), yield = 128 mg.

Combine the later, like fractions containing 3-hydroxy-1,3,5(10),6,8-19-nor-pregnapentaene-17α,21-diol-20-one 21-acetate as determined by thin layer chromatography, evaporate the combined fractions and crystallize the resultant residue from methanol to obtain 1,3,5(10),6,8,19-nor-pregnapentaene-3,17α,21-triol-20-one 21-acetate having physical data substantially the same as those set forth for this compound when prepared according to the procedure of Example 2, i.e. as set forth for product 3 in Example 2; yield = 1.43 gms. (58% theory).

EXAMPLE 8

16α-Methyl-1,3,5(10),6,8-19-Nor-Pregnapentaene-3,17α,21-Triol-11,20-Dione 3-Benzoate 21-Acetate To a solution of 9α-bromo-16α-methyl-1,4-pregnadiene-17α,21-diol-3,11,20-trione 21-acetate (30 gms.) in pyridine (240 ml.) add benzoyl chloride (60 ml.) and heat the reaction mixture at 60° C. for 20 hours, cool and pour into dilute hydrochloric acid. Extract the aqueous solution with ethyl acetate, wash the combined extracts with water, and evaporate. Chromatograph the resultant residue over silica gel eluting with petroleum ether/ether gradient. Combine the like fractions containing the desired product as determined by thin layer chromatography, evaporate, then crystallize the resultant residue from ether to obtain 16α-methyl-1,3,5(10),6,8-19-nor-pregnapentaene-3,17α,21-triol-11,20-dione 3-benzoate 21-acetate, yield 13.1 gms.; m.p. 183°–184°; [α]$_D^{26}$ +63° (dioxane); λ$_{max}^{methanol}$ 215 (ε = 40,600), 237 (ε = 38,400), 314 nm (ε = 7,900).

EXAMPLE 9

16α-Methyl-1,3,5(10),6,8-19-Nor-Pregnapentaene-3,17α,21-Triol-11,20-Dione

To a solution of 16α-methyl-1,3,5(10),6,8-19-nor-pregnapentaene-3,17α,21-triol-11,20-dione 3-benzoate 21-acetate (5 gms.) in methanol (250 ml.) add sodium bicarbonate (25 ml. of a 10% aqueous solution) and heat the reaction mixture at reflux temperature under an atmosphere of nitrogen for 2 hours. Cool the reaction mixture, evaporate the methanol in vacuo, dissolve the resultant residue in ethyl acetate, wash the ethyl acetate solution with water, then evaporate. Chromatograph the resultant residue over silica gel eluting with petroleum ether/ether gradient. Combine the like fractions containing the desired product as determined by thin layer chromatography and evaporate, then crystallize the resultant residue from ethyl acetate to obtain 16α-methyl-1,3,5(10),6,8-19-nor-pregnapentaene-3,17α,21-triol-11,20-dione.

EXAMPLE 10

Other Ester Derivatives of 16α-Methyl-1,3,5(10),6,8-19-Nor-Pregnapentaene-3,17α,21-Triol-11,20-Dione

A. The 21-Propionate and the 17-Propionate of 16α-Methyl-1,3,5(10),6,8-19-Nor-Pregnapentaene-3,17α,21-Triol-11,20-Dione To a solution of 16α-methyl-1,3,5(10),6,8-19-nor-pregnapentaene-3,17α,21-triol-11,20-dione (100 mg.) in dimethylsulfoxide (1.4 ml.) add triethylorthopropionate (0.14 ml.) and p-toluenesulfonic acid (14 mg.). Stir at room temperature for 5 hours, then add acetic acid/water (2 ml., 9:1) and continue stirring the reaction mixture for 20 hours. Pour the reaction mixture into aqueous sodium bicarbonate, extract with ethyl acetate, wash the combined extracts with water, then evaporate in vacuo. Chromatograph the resultant residue on 2 × 1000 mμ silica gel GF plates using a chloroform/ethyl acetate (3:1) solvent system. Visualize the plate under ultraviolet light and extract separately each of the two steroidal bands with ethyl acetate, and evaporate to residues yielding, respectively, 16α-methyl-1,3,5(10),6,8-19-nor-pregnapentaene-3,17α,21-triol-11,20-dione 21-propionate and 16α-methyl-1,3,5(10),6,8-19-nor-pregnapentaene-3,17α,21-triol-11,20-dione 17-propionate.

B. 16α-Methyl-1,3,5(10),6,8-19-Nor-Pregnapentaene-3,17α,21-Triol-11,20-Dione 3,17,21-Tripropionate To a suspension of 16α-methyl-1,3,5(10),6,8-19-nor-pregnapentaene-3,17α,21-triol-11,20-dione (2 gms.) in propionic acid (20 ml.) containing p-toluenesulfonic acid (200 mg.) at −5° C., add dropwise over a 40-minute period trifluoroacetic anhydride (8 ml.). Allow the reaction mixture to warm to room temperature, then stir for 24 hours. Pour the reaction mixture onto ice/water and extract with ethyl acetate. Wash the combined extracts with aqueous sodium bicarbonate, then with water and evaporate in vacuo. Chromatograph the resultant residue over silica gel eluting with petroleum ether/ether gradient. Combine the like fractions containing the desired product as determined by thin layer chromatography to obtain 16α-methyl-1,3,5(10),6,8-19-nor-pregnapentaene-3,17α,21-triol-11,20-dione 3,17,21-tripropionate.

C. 16α-Methyl-1,3,5(10)-6,8,-19-Nor-Pregnapentaene-3,17α,21-Triol-11,20-Dione 3,21-Diacetate To 16α-methyl-1,3,5(10),6,8-19-nor-pregnapentaene-3,17α,21-triol-11,20-dione (460 mg.) in pyridine (20 ml.) add acetic anhydride (2 ml.) and allow the reaction mixture to stay at room temperature for 4 hours. Pour the reaction mixture into dilute hydrochloric acid, extract with ethyl acetate, wash the combined extracts with water and evaporate in vacuo. Chromatograph the resultant residue over silica gel eluting with petroleum ether/ether gradient. Combine the like eluates as determined by thin layer chromatography to obtain 16α-methyl-1,3,5(10),6,8-19-nor-pregnapentaene-3,17α,21-triol-11,20-dione 3,21-diacetate.

D.
16α-Methyl-1,3,5(10),6,8-19-Nor-Pregnapentaene-3,17α,21-Triol-11,20-Dione 3,21-Dipropionate In the procedure of Example 10C, by utilizing an equivalent quantity of propionic anhydride instead of acetic anhydride, there is obtained 16α-methyl-1,3,5(10),6,8,-19-nor-pregnapentaene-3,17α,21-triol-11,20-dione 3,21-dipropionate.

EXAMPLE 11
16α-Methyl-1,3,5(10),6,8-19-Nor-Pregnapentaene-3,11β,17α,21-Tetrol-20-One 3,17,21-Tripropionate and its 11α-Hydroxy Epimer and the Corresponding 3-free Hydroxy Derivative To a solution of 16α-methyl-1,3,5(10),6,8-19-nor-pregnapentaene-3,17α,21-triol-11,20-dione 3,17,21-tripropionate (1 gm.) in tetrahydrofuran/methanol (50 ml., 1:1) (dried over an alumina column) at 0° C. add sodium borohydride (220 mg., 3 eq.) portionwise over a 5-minute period. Stir the reaction mixture for an additional 10 minutes, then bring to neutrality by adding glacial acetic acid dropwise. Pour the reaction mixture into water, extract with ethyl acetate, wash the combined extracts with water and evaporate. Chromatograph the resultant residue over silica gel GF column eluting with chloroform/ethyl acetate (9:1). Combine the like fractions as determined by thin layer chromatography, and evaporate each of the three different combined fractions to residues comprising, respectively, (1)  16α-methyl-1,3,5(10),6,8-19-nor-pregnapentaene-3,11α,17α,21-tetrol-20-one 3,17α,21-tripropionate, (2)  16α-methyl-1,3,5(10),6,8-19-nor-pregnapentaene-3,11β,17α,21-tetrol-20-one 3,17α,21-tripropionate. Purify by recrystallization from petroleum ether/ether, (3)  16α-methyl-1,3,5(10),6,8-19-nor-pregnapentaene-3,11β,17α,21-tetrol-20-one 17,21-dipropionate. Purify by recrystallizing from petroleum ether/ether.

EXAMPLE 12
6-Fluoro-16α-Methyl-1,3,5(10),6,8-19-Nor-Pregnapentaene-3,17α,21-Triol-20-One 21-Acetate Add 6α-fluoro-9α,11β-dichloro-16α-methyl-1,4-pregnadiene-17α,21-diol-3,20-dione 21-acetate (4.2 gms.) to refluxing dimethylformamide (200 ml.) and continue heating at reflux temperature for 30 minutes. Pour the reaction mixture into saturated aqueous sodium chloride, separate the resultant precipitate by filtration. Dissolve the precipitate in ethyl acetate, and fractionally crystallize to obtain 6α-fluoro-16α-methyl-1,4,8(14),9(11)-pregnatetraene-17α,21-diol-3,20-dione 21-acetate and 6-fluoro-16α-methyl-1,3,5(10),6,8-19-nor-pregnapentaene-3,17α,21-triol-20-one 21-acetate. Further purify the latter compound by crystallization from methylene chloride, yield 316 mg.; $[\alpha]_D^{26}+88.0°$ (dioxane); m.p. 238°–241° C.; $\lambda_{max}^{methanol}$ 238 ($\epsilon=50,500$), 270 ($\epsilon=5,000$), 281 ($\epsilon=5,000$), 293 ($\epsilon=3,400$), 315 sh ($\epsilon=1,700$), 330 ($\epsilon=2,400$), 344 nm ($\epsilon=2,600$).

EXAMPLE 13
16β-Methyl-1,3,5(10),6,8-19-Nor-Pregnapentaene-3,11β,17α,21-Tetrol-20-One 21-Acetate

A.
16β-Methyl-1,4,6,8-Pregnatetraene-11β,17α,21-Triol-3,20-Dione 21-Acetate To a mixture of 9α-chloro-16β-methyl-1,4,6-pregnatriene-11β,17α,21-triol-3,20-dione 21-acetate (3.44 gms.) in acetone (700 ml.) add potassium acetate (10.3 gms.) and reflux the reaction mixture with stirring for 48 hours. Filter the reaction mixture, evaporate the filtrate in vacuo to a low volume, pour into water and extract the aqueous mixture with ethyl acetate. Wash the combined organic extracts with water and evaporate to a volume of about 100 ml. Separate the resultant crystalline solid by filtration, and dry to obtain 16β-methyl-1,4,6,8-pregnatetraene-11β,17α,21-triol-3,20-dione 21-acetate, yield 1.96 gms.; m.p. 175°–180° C.; $[\alpha]_D^{26}+786°$ (pyridine); $\lambda_{max}^{methanol}$ 230 sh ($\epsilon=10,600$), 264 ($\epsilon=10,000$), 388 nm ($\epsilon=6,500$).

B.
16β-Methyl-1,3,5(10),6,8-19-Nor-Pregnapentaene-3,11β,17α,21-Tetrol-20-One 21-Acetate To a solution of 16β-methyl-1,4,6,8-pregnatetraene-11β,17α,21-triol-3,20-dione 21-acetate (850 mg.) in tetrahydrofuran (200 ml.) add 1 N hydrochloric acid (20 ml.). Stir the reaction mixture at room temperature for 1 hour, then pour the reaction mixture into 1 liter of saturated aqueous sodium chloride and extract with ethyl acetate. Wash the combined ethyl acetate extracts with water and evaporate to a volume of about 25 ml. Separate the resultant crystalline precipitate by filtration and dry to obtain 16β-methyl-1,3,5(10),6,8-19-nor-pregnapentaene-3,11β,17α,21-tetrol-20-one 21-acetate, yield 368 mg.; m.p. 203°–207° C.; $[\alpha]_D^{26}+172°$ (pyridine); $\lambda_{max}^{methanol}$ 233 ($\epsilon=69,100$), 267 ($\epsilon=4,800$), 278 ($\epsilon=5,400$), 315 ($\epsilon=1,900$), 327 ($\epsilon=2,300$), 340 nm ($\epsilon=2,700$).

EXAMPLE 14
16β-Methyl-1,3,5(10),6,8-19-Nor-Pregnapentaene-3,17α,21-Triol-11,20-Dione 21-Acetate

A.
16β-Methyl-1,4,6,8-Pregnatetraene-17α,21-Diol-3,11,20-Trione 21-Acetate To a solution of 16β-methyl-1,4,6,8-pregnatetraene-11β,17α,21-triol-3,20-dione 21-acetate (500 mg.) in methylene chloride (50 ml.) add finely powdered manganese dioxide (5 gms.), and stir at room temperature for 20 hours. Separate the manganese dioxide by filtration and wash with methylene chloride. Evaporate the combined filtrate and methylene chloride washings and crystallize the resultant residue from ether to yield 16β-methyl-1,4,6,8-pregnatetraene-17α,21-diol-3,11,20-trione 21-acetate; m.p. 185°–188° C., $\lambda_{max}^{methanol}$ 215 ($\epsilon=19,400$); 273 ($\epsilon=13,600$); 382 nm ($\epsilon=7,300$), $[\alpha]_D^{26}+1164°$ (CHCl$_3$).

B.
16β-Methyl-1,3,5(10),6,8-19-Nor-Pregnapentaene-3,17α,21-Triol-11,20-Dione 21-Acetate To a solution of 16β-methyl-1,4,6,8-pregnatetraene-17α,21-diol-3,11,20-trione 21-acetate (200 mg.) in tetrahydrofuran (50 ml.) add 1 N hydrochloric acid (5 ml.), and stir the reaction mixture for 1 hour. Pour into 500 ml. saturated aqueous sodium chloride and extract with ethyl acetate. Wash the combined extracts with saturated sodium chloride and evaporate to a volume of about 10 ml. Separate the resultant crystalline precipitate by filtration and dry to obtain 16β-methyl-1,3,5(10),6,8-19-nor-pregnapentaene-3,17α,21-triol-11,20-dione 21-acetate.

EXAMPLE 15

16α-Methyl-1,3,5(10),6,8-19-Nor-Pregnapentaene-3,11β,17α,21-Tetrol-20-One

A.

16α-Methyl-17α,20;20,21-Bismethylenedioxy-1,3,5(10),6,8-19-Nor-Pregnapentaene-3-Ol-11-One To a solution of 16α-methyl-1,3,5(10),6,8-19-nor-pregnapentaene-3,17α,21-triol-11,20-dione (4.3 gms.) in methylene chloride (200 ml.) under an atmosphere of nitrogen add formaldehyde (200 ml., 37% aqueous solution) and concentrated hydrochloric acid (200 ml.). Stir the mixture at room temperature for 4 hours, separate the two layers, extract the aqueous layer with methylene chloride, combine the organic layer and the methylene chloride extracts and wash with aqueous sodium bicarbonate, then with water. Evaporate the organic solution and chromatograph the resultant residue over silica gel eluting with a petroleum ether/ether gradient. Combine the like fractions containing the desired product as determined by thin layer chromatography and evaporate and crystallize the resultant residue from ether to obtain 16α-methyl-17α,20;20,21-bismethylenedioxy-1,3,5(10)-6,8-19-nor-pregnapentaene-3-ol-11-one.

B.

16α-Methyl-17α,20;20,21-Bismethylenedioxy-1,3,5(10),6,8-19-Nor-Pregnapentanene-3,11β-Diol To a solution of 16α-methyl-17α,20;20,21-bismethylenedioxy-1,3,5(10),6,8-19-nor-pregnapentaene-3-ol-11-one (2 gms.) in tetrahydrofuran:methanol (100 ml., 1:1) dried over alumina at 0° C., add sodium borohydride (3 equivalents, 575 mg.) in portions over a 5-minute period. Stir the reaction mixture for an additional 15 minutes, then add glacial acetic acid dropwise until the solution is neutral. Pour the reaction mixture into water, extract with ethyl acetate, wash the combined extracts with water and evaporate. Chromatograph the resultant residue over silica gel eluting with chloroform-ethyl acetate gradient. Combine the like eluates as determined by thin layer chromatography to obtain 16α-methyl-17α,20;20,21-bismethylenedioxy-1,3,5(10),6,8-19-nor-pregnapentaene-3,11α-diol (from the combined early fractions) and 16α-methyl-17α,20;20,21-bismethylenedioxy-1,3,5(10),6,8-19-nor-pregnapentaene-3,11β-diol (from the combined like later fractions). Purify by crystallization from ether.

C.

16α-Methyl-1,3,5(10),6,8-19-Nor-Pregnapentaene-3,11β,17α,21-Tetrol 20-One

Add 16α-methyl-17α,20;20,21-bismethylenedioxy-1,3,5(10,6,8-19-nor-pregnapentaene-3,11β-diol (990 mg., 2.5 mmol) to aqueous 45% hydrofluoric acid (2.5 ml.) at 0° C. and stir the resulting suspension at 0° C. for 1.5 hours. Bring the reaction mixture to neutrality by adding aqueous 5% potassium bicarbonate, then extract with ethyl acetate, wash the combined extracts with water and evaporate to a small volume. Separate the 16α-methyl-1,3,5(10),6,8-19-nor-pregnapentaene-3,11β,17α,21-tetrol 20one.

EXAMPLE 16

16α-Methyl-1,3,5(10),6,8-19-Nor-Pregnapentaene-3,11β,17α,21-Tetrol-20-One

To a solution of 16α-methyl-1,3,5(10),6,8-19-nor-pregnapentaene-3,11β,17α,21-tetrol-20-one, 3,17α,21-tripropionate (271 mg.) in methanol (25 ml.) add sodium bicarbonate (3.0 ml., 5% aqueous solution) and stir overnight at room temperature. Add dilute hydrochloric acid until the reaction mixture is at about pH 7, then remove the methanol in vacuo. Add water to the resultant residue and extract with ether. Wash the combined ether extracts with water, dry over magnesium sulfate and evaporate. Crystallize the resultant residue from methylene chloride/ether to obtain 16α-methyl-1,3,5(10),6,8-19-nor-pregnapentaene-3,11β,17α,21-tetrol-20-one.

We claim:

1. The method of eliciting a mitotic inhibitory response in a warm-blooded animal having a disease characterized by rapid cell proliferation which comprises administering to said animal a non-toxic, mitotic inhibitory effective amount of a 19-nor-pregnapentaene-20-one of the following formula I:

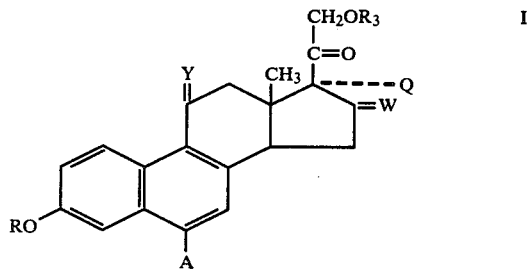

wherein

A is hydrogen, lower alkyl, fluoro, fluoromethyl, difluoromethyl, or trifluoromethyl;

R is hydrogen, lower alkyl, or an acyl radical of a hydrocarboncarboxylic acid having up to 20 carbon atoms;

Y is (H,H), (H,OH), or oxygen,

W is (H,H); (H, lower alkyl); (Hα-hydroxy); (H,α-OR₁), wherein R₁ is an acyl radical of a hydrocarboncarboxylic acid having up to 20 carbon atoms; or =CHT wherein T is hydrogen, lower alkyl, fluorine, or chlorine;

Q is OR₂ wherein R₂ is hydrogen or an acyl radical of a hydrocarboncarboxylic acid having up to 20 carbon atoms; hydrogen provided W is (H,H), or (H, lower alkyl); or Q and W together is a ≠α,17α-lower alkylidenedioxy;

R₃ is hydrogen or an acyl radical of a hydrocarboncarboxylic acid having up to 20 carbon atoms; or OR₃ together with Q is a member selected from the group consisting of alkylidenedioxy and alkylorthoalkanoate;

and when Q is hydroxy and R₃ is hydrogen, the 17α,20;20,21-bismethylenedioxy derivatives thereof;

together with a non-toxic pharmaceutically acceptable carrier.

2. The method of claim 1 wherein said disease is a skin disease characterized by rapid cell proliferation.

3. The method of claim 2 when said 19-nor-pregnapentaene-20-one is administered topically, which is the method of reducing epidermal mitosis in a warm-blooded animal having a skin disease characterized by rapid cell proliferation which comprises applying topically to the affected area in a concentration effective for reducing epidermal mitosis, a 19-nor-pregnapentaene-20-one of formula I in claim 1, together with a non-toxic, pharmaceutically acceptable carrier.

4. The method of claim 3 wherein said skin disease is psoriasis, which is the method of treating and controlling psoriasis which comprises applying topically to the affected area in a concentration effective for the treatment of psoriasis, a 19-nor-pregnapentaene-20-one of formula I in claim 1, together with a non-toxic, pharmaceutically acceptable carrier.

5. The method of claim 4, when carried out with a 1,3,5(10),6,8-19-nor-pregnapentaene-20-one of formula I wherein W is (H, lower alkyl) or (H,H).

6. The method of claim 5 when carried out with a compound of structural formula II:

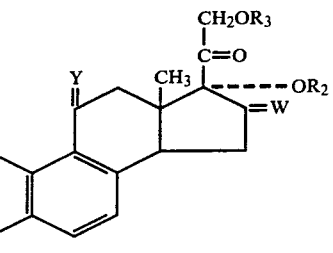

wherein
R is hydrogen, lower alkyl, or an acyl radical of a hydrocarboncarboxylic acid having up to 20 carbon atoms;
$R_2$ and $R_3$ are each hydrogen or an acyl radical of a hydrocarboncarboxylic acid having up to 20 carbon atoms;
Y is (H, OH) or oxygen; and
W is (H,H) or (H, methyl).

7. The method of claim 6 when carried out with 1,3,5(10),6,8-19-nor-prognapentaene-3,17α,21-triol-11,20-dione or with the 21-acetate thereof or their 16α-methyl or 16β-methyl homologs.

8. A topical pharmaceutical composition for the treatment of psoriasis comprising an anti-psoriatically effective amount of a 19-nor-pregnapentaene-20-one of formula I in claim 1, together with a non-toxic, pharmaceutically acceptable carrier.

9. A topical pharmaceutical composition of claim 8 wherein said 19-nor-pregnapentaene-20-one is a 19-nor-pregnapentaene-20-one of formula II in claim 6.

10. The topical pharmaceutical composition of claim 9 comprising an anti-psoriatic effective amount of 1,3,5(10),6,8-19-nor-pregnapentaene-3,17α,21-triol-11,20-dione or of the 21-acetate thereof or of their 16β-methyl or 16α-methyl homologs, together with a non-toxic, pharmaceutically acceptable carrier.

* * * * *

UNITED STATES PATENT AND TRADEMARK OFFICE
CERTIFICATE OF CORRECTION

PATENT NO. : 4,185,101

DATED : January 22, 1980

INVENTOR(S) : Richard W. Draper et al

It is certified that error appears in the above-identified patent and that said Letters Patent are hereby corrected as shown below:

Claim 1, column 22, line 56, "≠α,17α-" should read ---16α,17α---.

Signed and Sealed this

Fifth Day of August 1980

[SEAL]

*Attest:*

*Attesting Officer*

SIDNEY A. DIAMOND

*Commissioner of Patents and Trademarks*